(12) United States Patent
Kokuryo et al.

(10) Patent No.: US 7,507,982 B2
(45) Date of Patent: Mar. 24, 2009

(54) RAIN SENSOR WITH AMBIENT LIGHT COMPENSATION

(75) Inventors: Kazuto Kokuryo, Ohtsu (JP); Keitaro Iguchi, Ohtsu (JP); Yoshiteru Makino, Ohtsu (JP)

(73) Assignee: Niles Co. Ltd., Tokyo (JP)

( * ) Notice: Subject to any disclaimer, the term of this patent is extended or adjusted under 35 U.S.C. 154(b) by 82 days.

(21) Appl. No.: 10/556,828

(22) PCT Filed: May 13, 2004

(86) PCT No.: PCT/JP2004/006758

§ 371 (c)(1),
(2), (4) Date: Jan. 29, 2007

(87) PCT Pub. No.: WO2004/102168

PCT Pub. Date: Nov. 25, 2004

(65) Prior Publication Data

US 2007/0138868 A1 Jun. 21, 2007

(30) Foreign Application Priority Data

May 15, 2003 (JP) ............................. 2003-136866
May 15, 2003 (JP) ............................. 2003-136906

(51) Int. Cl.
*G01N 15/06* (2006.01)
*G01N 21/49* (2006.01)
*G01N 21/85* (2006.01)

(52) U.S. Cl. ............... 250/573; 250/214 SW; 340/619

(58) Field of Classification Search ............ 250/214 R, 250/214.1, 214 AL, 214 C, 214 B, 573, 574, 250/577, 214 DC, 214 SW; 340/618–619
See application file for complete search history.

(56) References Cited

U.S. PATENT DOCUMENTS 6,066,843 A * 5/2000 Scheremeta ............ 250/214 AL (Continued)

FOREIGN PATENT DOCUMENTS

JP 60-117930 A 6/1985

(Continued)

OTHER PUBLICATIONS

Microfilm of the specification and dwgs. Annexed to the request of Japanese Utility Model App. No. 70280/1987 (laid-open No. 181840/1988), Advantest Corp., Nov. 24, 1988, Full Text.

*Primary Examiner*—Georgia Y Epps
*Assistant Examiner*—Francis M Legasse, Jr.
(74) *Attorney, Agent, or Firm*—RatnerPrestia

(57) ABSTRACT

A signal processing circuit provided with an outside-light component reducing circuit capable of reducing an outside light component in the frequency separation method is provided. This is a signal detecting circuit which irradiates a pulse light from an LED to a windshield of a vehicle, receives a reflected light by a PD, processes the pulse signal from the PD and inputs it to a processing unit in order to automatically control a wiper for eliminating raindrops on the windshield of the vehicle. This is provided with a current—voltage converter circuit for converting the pulse signal from the LED to a voltage signal, an outside-light component reducing circuit provided in parallel with the current—voltage converter circuit for reducing the outside light component included in the output signal of the current—voltage converter circuit and a band-pass filter circuit/amplifier circuit for reducing the noise in the output signal of the current—voltage converter circuit and amplifying the output signal.

6 Claims, 22 Drawing Sheets

U.S. PATENT DOCUMENTS 6,281,640 B1 * 8/2001 Kim .......................... 315/291
6,331,819 B1 * 12/2001 Hog .......................... 340/604
6,573,490 B2 * 6/2003 Hochstein .............. 250/227.25

FOREIGN PATENT DOCUMENTS

| | | |
|---|---|---|
| JP | 63-273021 A | 11/1988 |
| JP | 64-20418 A | 1/1989 |
| JP | 64-68030 A | 3/1989 |
| JP | 2-189444 A | 7/1990 |
| JP | 3-264828 A | 11/1991 |
| JP | 4-134224 A | 5/1992 |
| JP | 4-283970 A | 10/1992 |
| JP | 5-264347 A | 10/1993 |
| JP | 11-148864 A | 6/1999 |
| JP | 2000-341055 A | 12/2000 |
| JP | 2002-277386 A | 9/2002 |

* cited by examiner

RAIN SENSOR WITH AMBIENT LIGHT COMPENSATION

FIELD OF THE INVENTION

The present invention relates to a signal detecting circuit of a rain sensor, which is a rain-drop detecting device for automatically controlling a wiper for eliminating rain drops or the like on a windshield of a vehicle, and particularly to a signal detecting circuit in which an outside-light component reducing circuit is provided. And the present invention further relates to particularly to a method for reducing an outside light component in a rain sensor.

BACKGROUND ART

A rain sensor lights a light emitting element such as a light emitting diode (LED) at a regular frequency, irradiates the light from the light emitting element to a windshield (front glass), receives a reflected light by a light receiving element such as a photodiode (PD), takes in an output signal (pulse signal) of the PD in a microcomputer and finally measures a rainfall level by detecting raindrops or an adhesion amount of raindrops.

FIG. 1 shows a signal detecting mechanism of the rain sensor. A light 11 from an LED 10 goes through lenses 12 and a prism 14 and is reflected by the surface of a front glass 16, goes through a prism 14 and a lens 18 and enters a PD 20.

A signal detecting circuit for detecting a pulse signal outputted by the PD 20 is, as shown in FIG. 2, comprised by an analog circuit and a microcomputer. The analog circuit 22 is comprised by a current—voltage (I-V) converter circuit 24, a band-pass filter circuit/amplifier circuit 26 and a peak hold circuit 30. The pulse signal obtained from the PD 20 is converted by the I-V converter circuit 24 from change of a current value to a change of a voltage value. A noise component is eliminated and amplified by the band-pass filter circuit/amplifier circuit 26 and finally, a peak of the amplified pulse signal is held by the peak hold circuit 30. The held peak value is sent to a microcomputer 32.

The microcomputer 32 is provided with an A/D converter 34 and processes a digital value obtained from the A/D converter with software to obtain raindrop information. The rainfall level is determined from the raindrop information.

With the rain sensor with the structure shown in FIG. 1, the light received by the PD 20 includes not only the reflected light from the LED 10 but also, as shown in FIG. 3, light from the outside environment, that is, an outside light 13, and about as much as 90% of the light received by the PD is this outside light component. The components of the outside light include those with approximately constant light intensity and those with fluctuating light intensity. Hereinafter, those with constant light intensity will be referred to as a constant outside-light component and those with fluctuating light intensity as a fluctuating outside-light component.

FIG. 4 shows an output waveform of the I-V conversion circuit 24 with the constant outside-light component. It is understood that the PD pulse signal is overlapped on the constant outside light component. A bias voltage level is a voltage level when the PD 20 is operated by a reverse bias.

FIG. 5 shows an output waveform of the I-V conversion circuit 24 with the fluctuating outside-light component. It is understood that the PD pulse signal is overlapped on the fluctuating outside-light component.

If the constant outside-light component is included in the outside light 13, as shown in FIG. 6, the voltage of the pulse signal outputted by the PD 20 is raised by the outside light component. When it exceeds a saturation voltage of an operational amplifier of the I-V conversion circuit 24, the signal component is crushed and a correct signal level is not inputted into the A/D converter 34. Therefore, such a problem is caused that a correct rainfall level cannot be determined.

On the other hand, if the fluctuating outside-light component is included in the outside light, and its frequency band comes into a pass band of the band-pass filter circuit/amplifier circuit 26, a high frequency component of the fluctuating outside light passes through the band-pass filter circuit/amplifier circuit 26 and as a result, the S/N ratio of an output value of the peak hold circuit 30 is deteriorated. The microcomputer 32 cannot determine the correct rainfall level, which is a problem.

There are the following two methods to reduce the above outside light component including the constant outside-light component and the fluctuating outside-light component.

The first method is a method using a visible-light cutting (absorbing) prism as the prism 14 shown in FIG. 1. With this method, however, the reflected light from the LED is also attenuated by the visible-light cutting (absorbing) prism, and the signal received by the PD is lowered, which is a problem.

The second method for reducing the outside-light component is a method for cutting the outside-light component by increasing the number of reflections in the prism 14 to prevent the outside light from directly entering the light receiving element. With this method, however, the size of the prism is increased and hence, the size of the rain sensor itself is increased, which is a problem.

DISCLOSURE OF THE INVENTION

Therefore, an object of the present invention is to provide a signal detecting circuit provided with an outside-light component reducing circuit which can reduce an outside light component by electric treatment, not using the above-mentioned conventional methods.

Another object of the present invention is to provide a signal detecting method including reduction of the outside light component.

Still another object of the present invention is to provide a method for reducing the outside light component in a signal detecting circuit for a rain sensor and an outside-light component reducing circuit.

The present invention is a signal detecting circuit which irradiates a pulse light from a light emitting element to a windshield of a vehicle, receives a reflected light by a light receiving element, processes the pulse signal from the light receiving element and inputs it to a processing unit in order to control a wiper of the vehicle, provided with a current—voltage converter circuit for converting the pulse signal from the light emitting element to a voltage signal, an outside-light component reducing circuit provided in parallel with the current—voltage converter circuit for reducing an outside light component included in an output signal of the current—voltage converter circuit, and a band-pass filter circuit/amplifier circuit for reducing a noise of the output signal of the current—voltage converter circuit and for amplifying the output signal.

The present invention is also a signal detecting method which irradiates a pulse light from a light emitting element to a windshield of a vehicle, receives a reflected light by a light receiving element, processes the pulse signal from the light emitting element and inputs it to a processing unit in order to control a wiper of the vehicle, comprising a step of converting the pulse signal from the above light emitting element to a voltage signal, a step of reducing an outside light component included in the above voltage signal converted as above, and a step of reducing a noise of the above voltage signal and amplifying the voltage signal.

The present invention is moreover an outside-light component reducing circuit for reducing the outside light component in a signal detecting circuit which irradiates a pulse light from a light emitting element to a windshield of a vehicle, receives a reflected light by a light receiving element, processes the pulse signal from the light emitting element and inputs it to a processing unit in order to control a wiper of the vehicle.

One embodiment of such an outside-light component reducing circuit is an outside-light component reducing circuit provided in parallel with a current—voltage converter circuit for converting a pulse signal from a light emitting element to a voltage signal, for frequency-separating the outside light component included in an output signal of the current—voltage converter circuit and feeding back to the input side of the current—voltage converter circuit.

Another embodiment of the outside-light component reducing circuit is an outside-light component reducing circuit provided in parallel with a current—voltage converter circuit for converting a pulse signal from a light receiving element to a voltage signal, for holding the outside light component included in an output signal of the current—voltage converter circuit and feeding it back to the input side of the current—voltage converter circuit.

BRIEF DESCRIPTION OF THE DRAWINGS

FIG. 16 is a diagram for explaining presence of taking-in of an outside light component voltage by turning a switch circuit on.

BEST MODE FOR CARRYING-OUT OF THE INVENTION

FIRST PREFERRED EMBODIMENT

Figure 1:
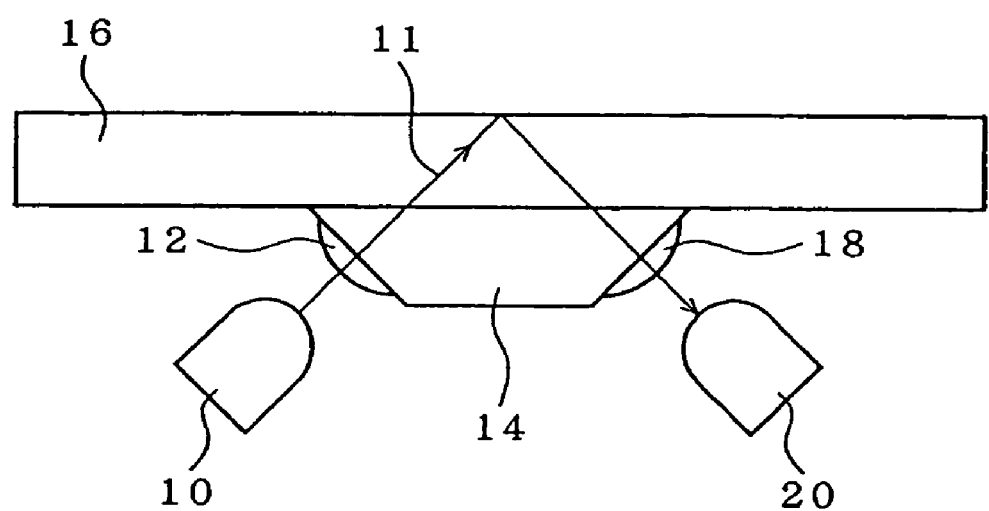
FIG. 1 is a diagram showing a signal detecting mechanism of a rain sensor.
Figure 2:
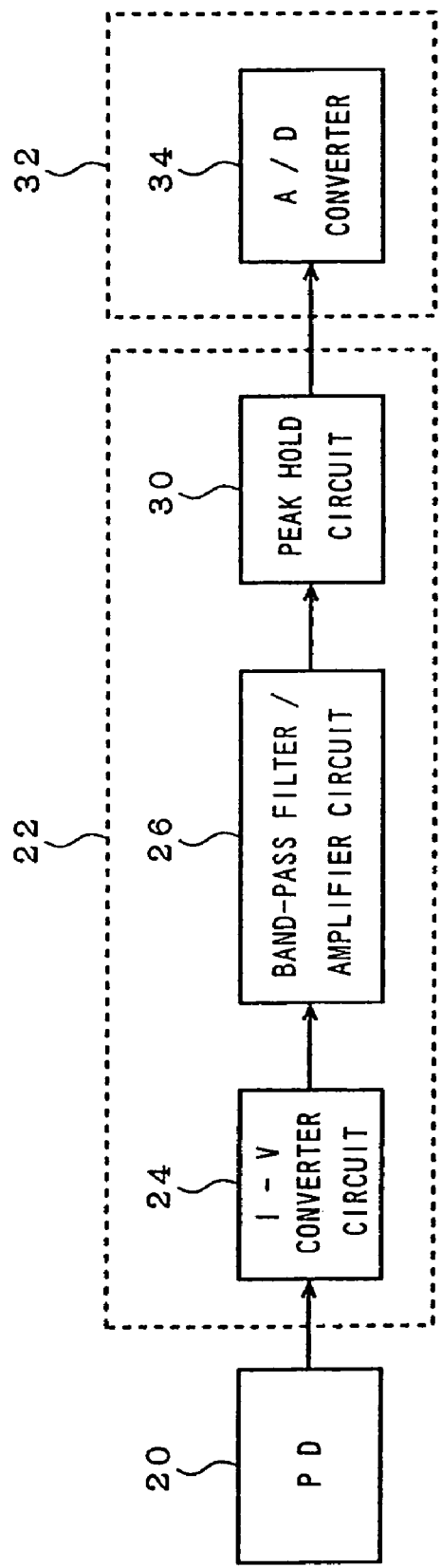
FIG. 2 is a diagram showing a conventional signal detecting circuit.
Figure 3:
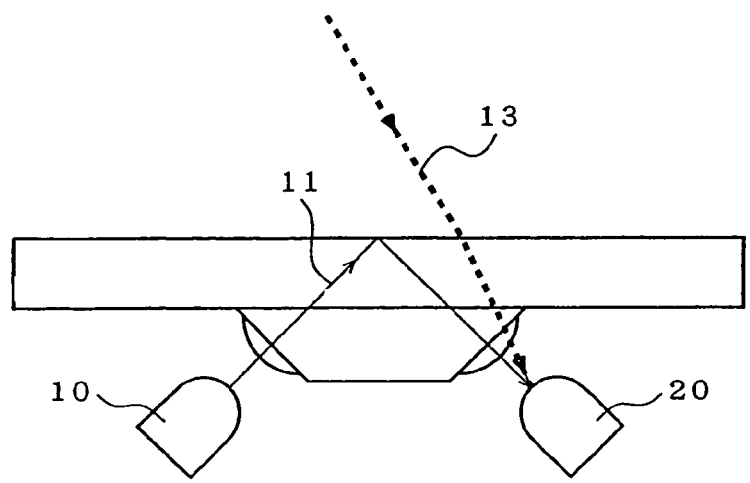
FIG. 3 is a diagram showing incidence of an outside light into the rain sensor.
Figure 4:
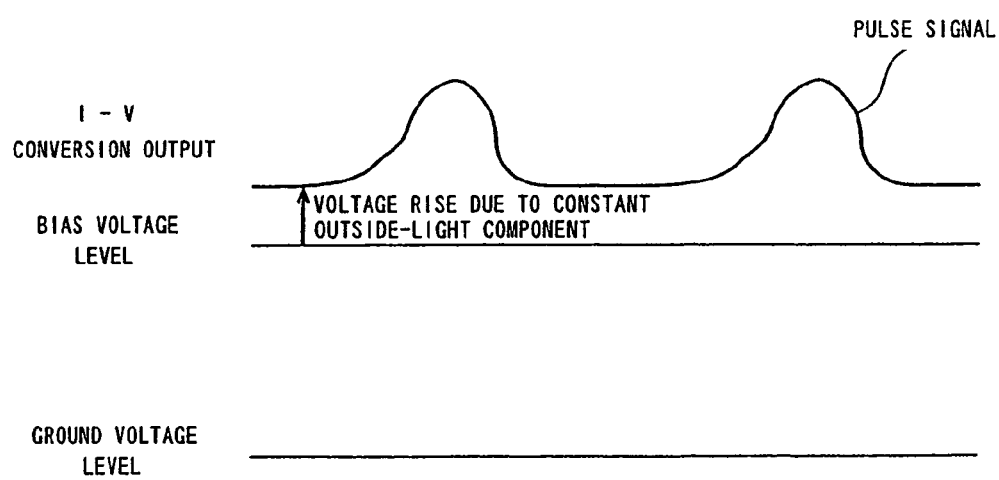
FIG. 4 is a diagram showing a pulse signal waveform from a PD when a constant outside-light component exists.
Figure 7:
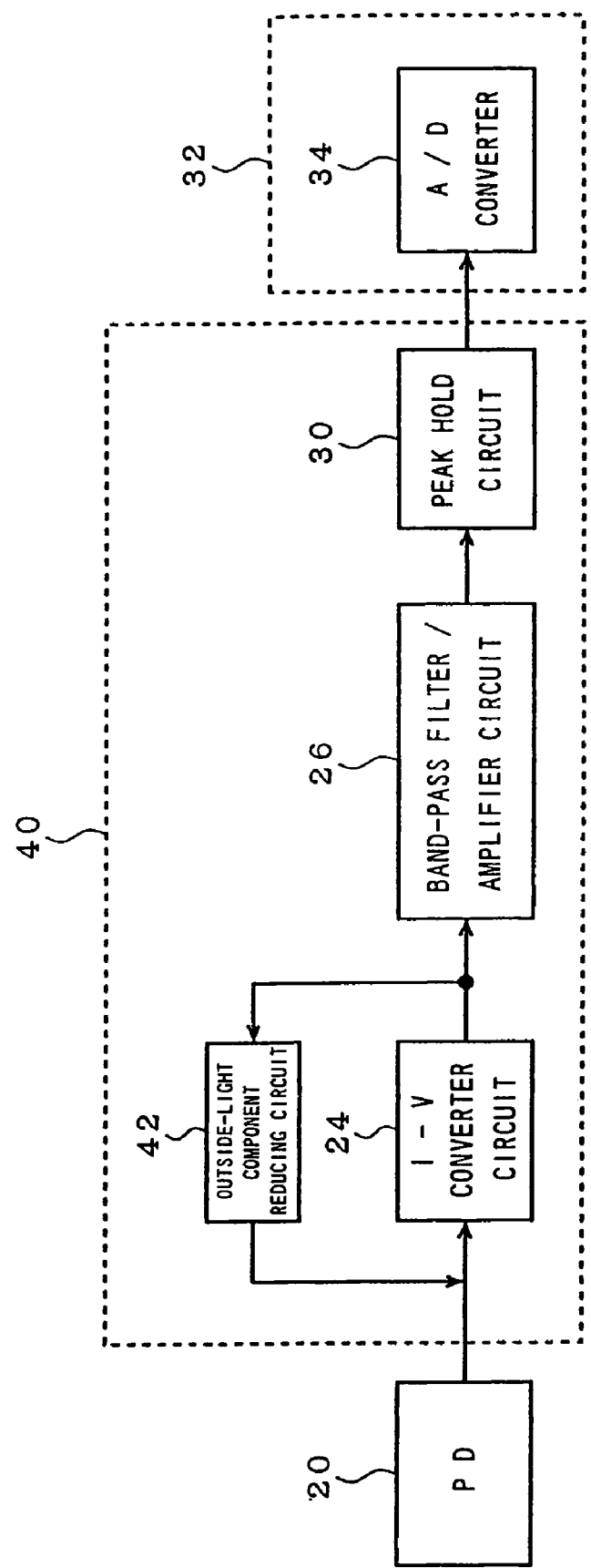
FIG. 7 is a block diagram showing a signal detecting circuit using an outside-light component reducing circuit of the present invention.

FIG. 7 is a block diagram showing a first preferred embodiment of a signal detecting circuit including an analog circuit 40 using the outside-light component reducing circuit of the present invention. In the conventional signal detecting circuit in FIG. 2, the outside-light component reducing circuit 42 is inserted in parallel with the I-V converter circuit 24.

Figure 8:
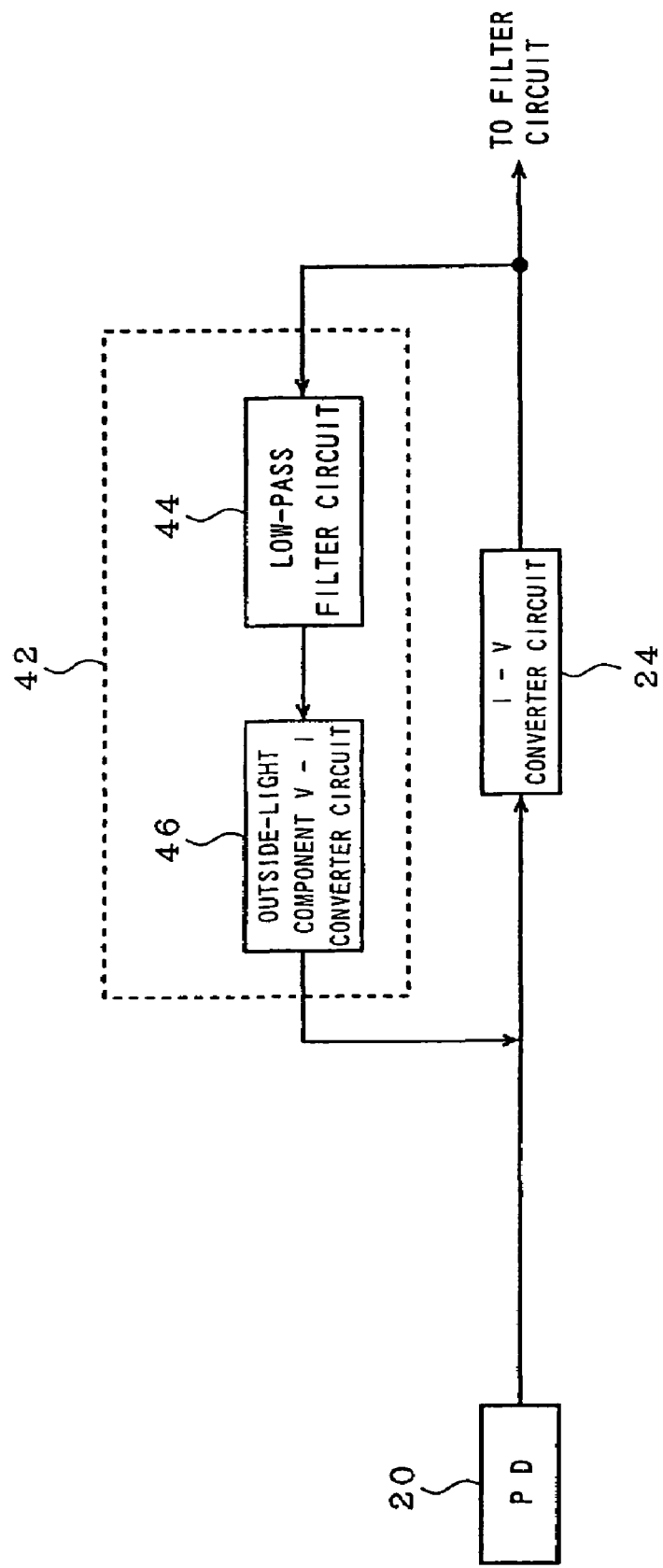
FIG. 8 is a block diagram showing the configuration of the outside-light component reducing circuit.

FIG. 8 is a block diagram showing the configuration of the outside-light component reducing circuit 42. The outside-light component reducing circuit is comprised by a low-pass filter circuit 44 and an outside-light component voltage-current (V-I) converter circuit 46.

Figure 9:
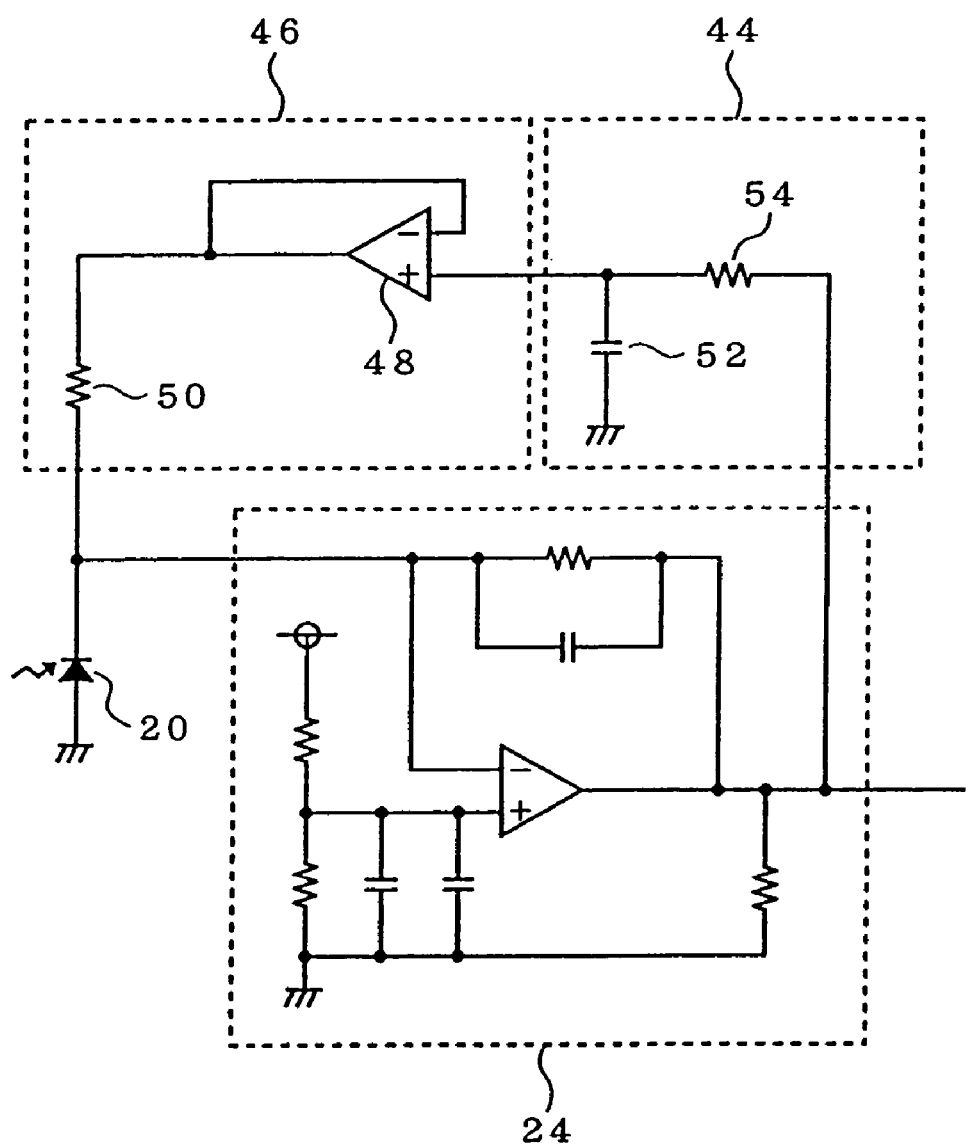
FIG. 9 is a diagram showing a concrete circuit configuration of the outside-light component reducing circuit.

FIG. 9 shows a concrete circuit configuration of the outside-light component reducing circuit. The outside-light component V-I converter circuit 46 is comprised by an operational amplifier 48 and a feedback resister 50. The low-pass filter circuit 44 is comprised of a capacitor 52 and a resistor 54.

Figure 10:
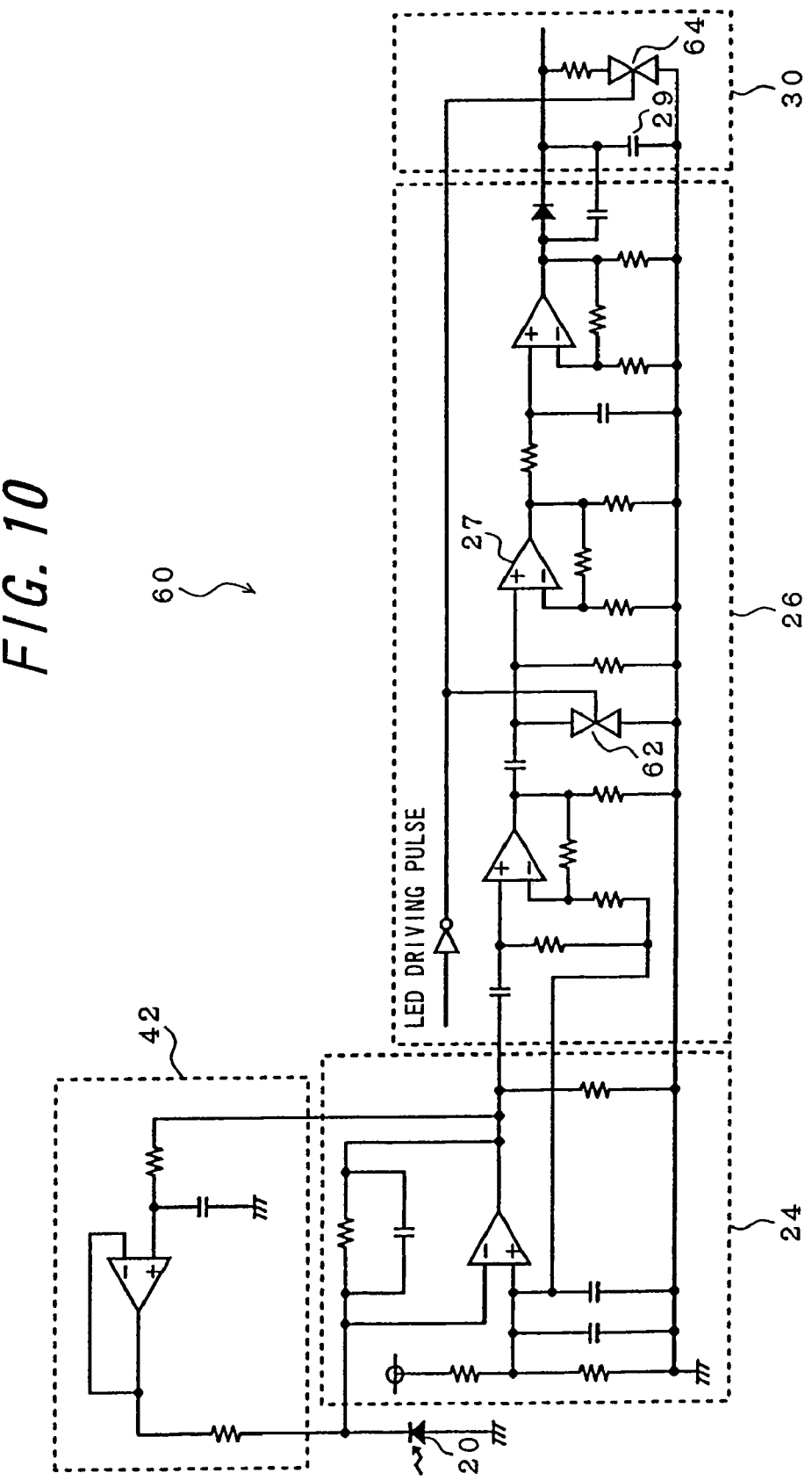
FIG. 10 is a concrete circuit diagram of a signal detecting circuit provided with the outside-light component reducing circuit shown in FIG. 8.

FIG. 10 is a concrete circuit diagram of a signal detecting circuit 60 provided with the outside-light component reducing circuit 42 shown in FIG. 9.

The band-pass filter circuit/amplifier circuit 26 is provided with a switching element 62, and the peak hold circuit 30 is also provided with a switching element 64. On/off of these switching elements 62, 64 are controlled by an LED lighting/driving pulse, which will be described later.

Operation of the switching element 62 of the band-pass filter circuit/amplifier circuit 26 will be described. The pulse signal outputted from the I-V converter circuit 24 is overlapped on the bias voltage. The high-pass filter prior to the switching element 62 is connected to the ground. After passing through the high-pass filter, an inclination component (high-frequency component) is outputted and as a result, the output value might be lowered below the ground, that is, negative. If the negative output value drops below the lower limit value of an input voltage range of the operational amplifier 27 when a negative output value is inputted to the operational amplifier 27 of the band-pass filter circuit/amplifier circuit 26, it might destroy the operational amplifier. In order to prevent this, only when the LED driving pulse is at H level, that is, only during the period of the pulse signal, the switching element 62 is turned off so that the negative output value after the period of pulse signal is not applied to the operational amplifier 27.

The switching element 64 of the peak hold circuit 30 acts to discharge electricity of the capacitor 29 when turned on for preparation of the next peak hold operation.

Figure 11:
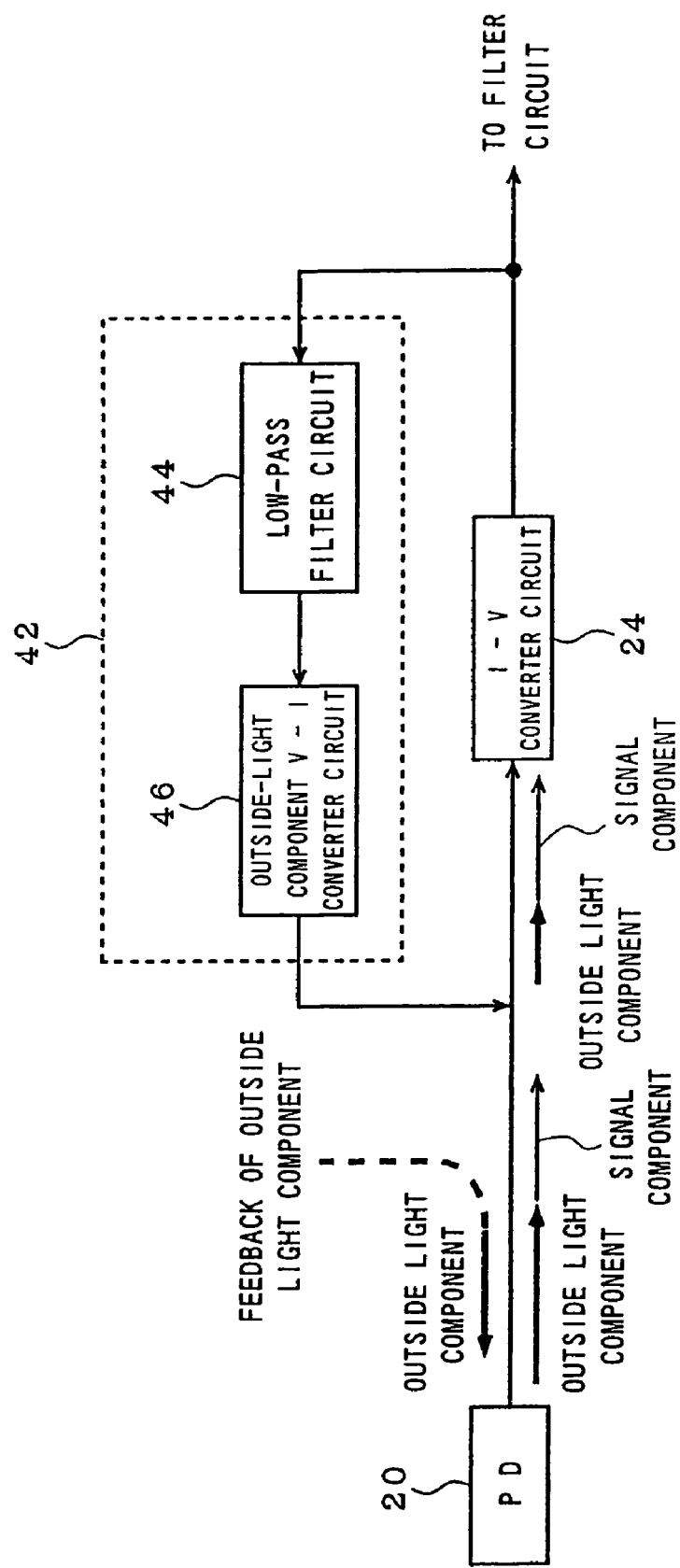
FIG. 11 is a diagram for explaining operation of the outside-light component reducing circuit.

Next, operation of the outside-light component reducing circuit 42 will be described. FIG. 11 is a diagram for explaining an outline of the operation. The outside-light component reducing circuit 42 performs feedback of the outside light component (constant outside-light component and fluctuating outside-light component) all the time whether the LED is lighted or not.

Figure 12:
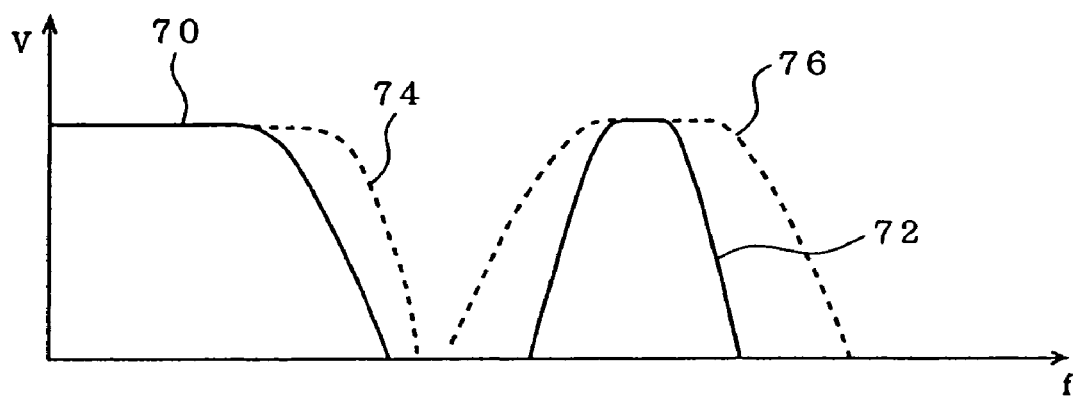
FIG. 12 is a graph showing a relationship between the band of the outside light component and a signal pass band of a low-pass filter circuit.

FIG. 12 shows the relationship between the frequency band of the outside light component passed by the low-pass filter circuit 44 and the frequency band of the band-pass filter circuit passing the PD pulse signal. In this Fig., the PD pulse signal band is also shown. The vertical axis indicates the intensity of a signal component (V) and the horizontal axis for a frequency (f).

70 shows the band of the outside light component and 72 for the band of the PD pulse signal. The band 74 of the low-pass filter circuit 44 of the outside-light component reducing circuit 42 covers the band 70 of the outside light component. Therefore, the constant outside light component and the fluctuating outside light component pass through the low-pass filter circuit 44 of the outside light component reducing circuit 42 and are inputted to the outside-light component V-I converter circuit 46. The outside-light component V-I converter circuit 46 coverts this to an electric current and feeds it back to the input side of the I-V converter circuit 24. The fed-back outside-light component current flows in the direction opposite to the pulse signal current from the PD, and the outside light component is reduced. As a result, to the input of the I-V converter circuit 24, (reduced outside light component)+(signal component) are inputted.

The signal component from the I-V converter circuit 24 is sent to the band-pass filter circuit/amplifier circuit 26.

As shown in FIG. 12, the band 76 of the band-pass filter circuit/amplifier circuit 26 covers the PD pulse signal band 72, and a noise is removed. After the noise is removed, the component is amplified by the band-pass filter circuit/amplifier circuit 26, and the peak value is held at the peak hold circuit 30. The peak value is inputted to the A/D converter 34 of the microcomputer 32.

By providing the outside-light component reducing circuit in this way, the constant outside light component and the fluctuating outside light component can be reduced. Since the constant outside-light component is reduced, output of the I-V converter circuit is not saturated. Also, since the fluctuating outside-light component is reduced, the S/N ratio can be improved.

SECOND PREFERRED EMBODIMENT

A second preferred embodiment of a signal detecting circuit including an analog circuit using an outside-light component reducing circuit different from the first preferred embodiment will be described.

Figure 13:
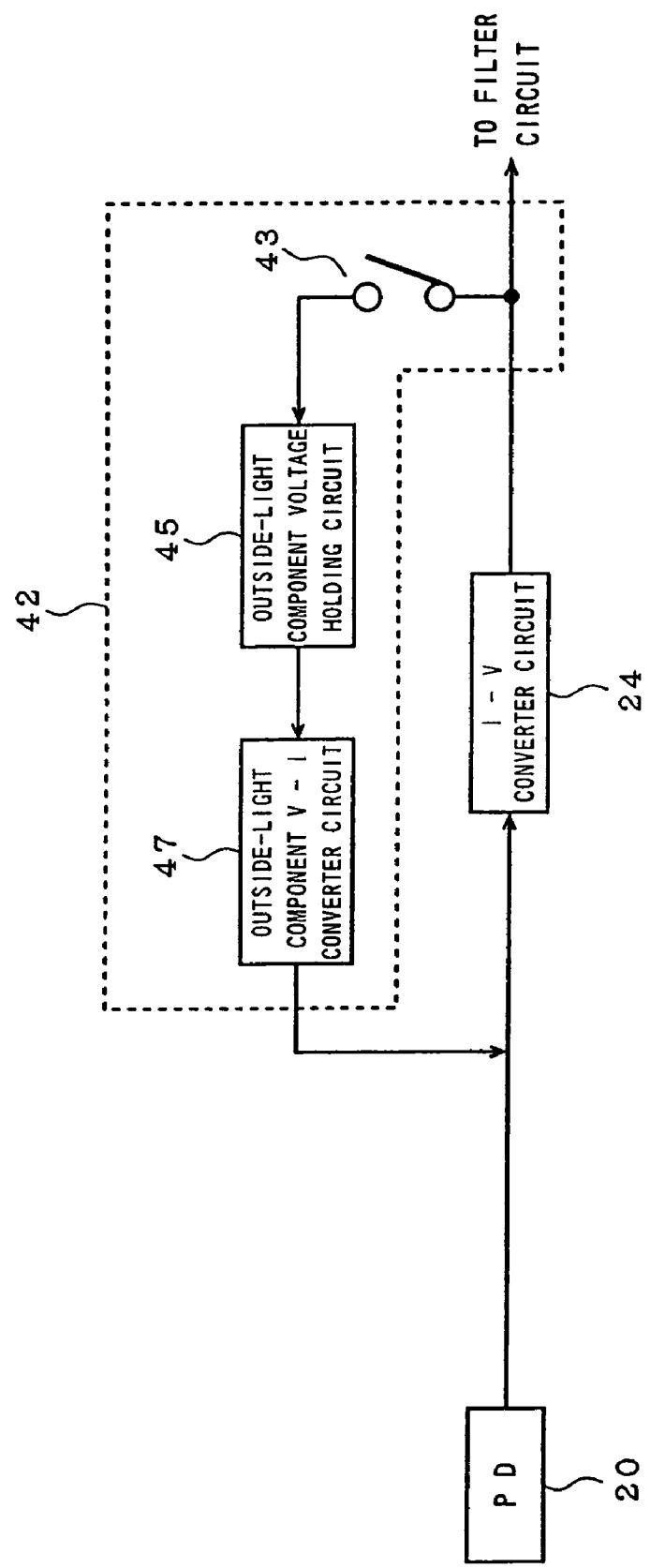
FIG. 13 is a block diagram showing another configuration of the outside-light component reducing circuit.

Except that the construction of the outside-light component reducing circuit is different, it is the same as the circuit in FIG. 7. The construction of an outside-light component reducing circuit 42 according to this preferred embodiment is shown in FIG. 13. The outside-light component reducing circuit 42 is comprised by an outside-light component voltage holding circuit 45, and outside-light component V-I converter circuit 47 and a feedback switch circuit 43.

Figure 14:
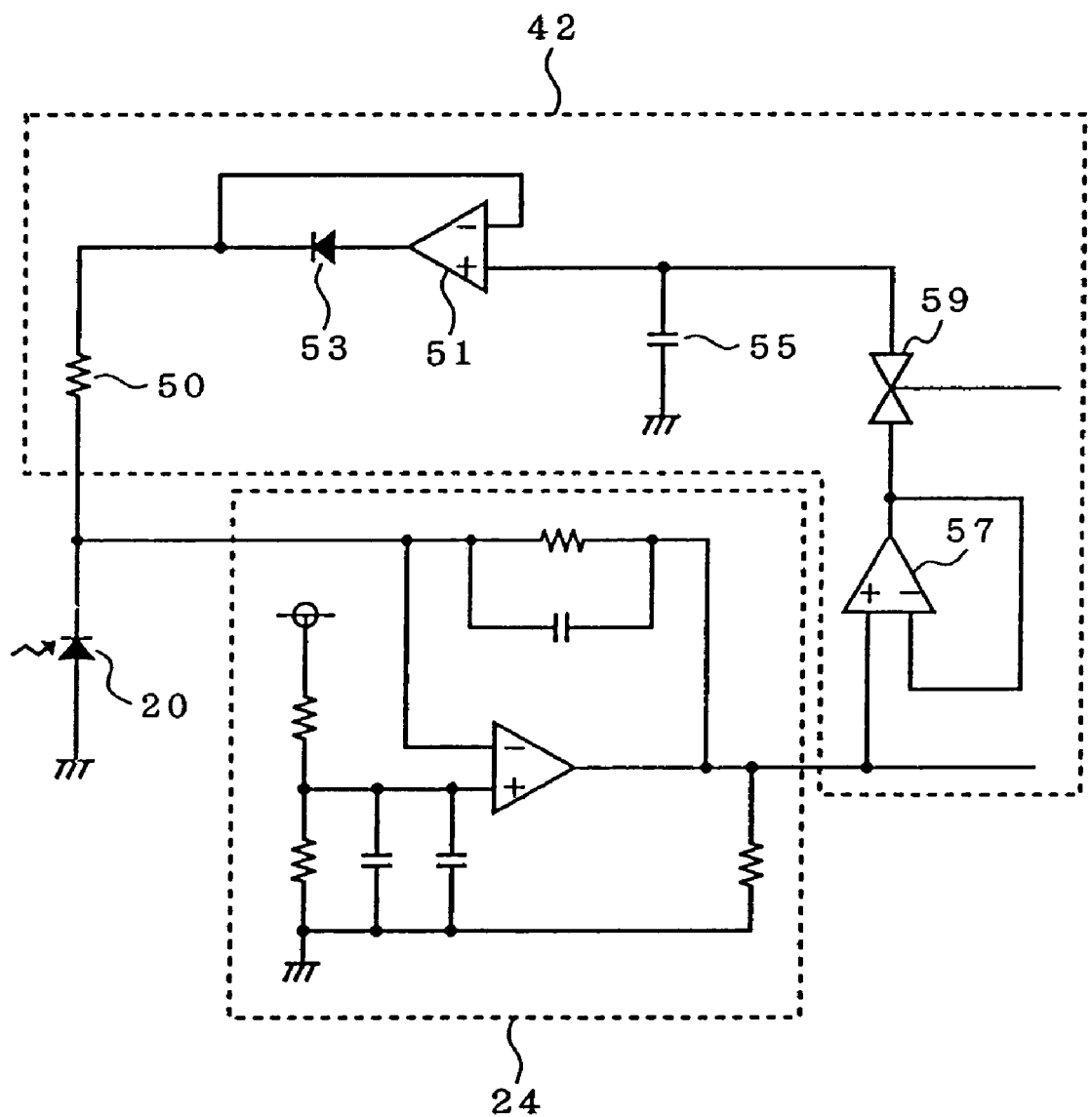
FIG. 14 is a diagram showing a concrete circuit configuration of the outside-light component reducing circuit.

FIG. 14 shows a concrete circuit configuration of the outside-light component reducing circuit 42. The outside-light component V-I converter circuit 47 is comprised by an operational amplifier 51, a diode 53 and a feedback resistor 50. The outside-light component voltage holding circuit 45 is comprised by a capacitor 55. The feedback switch circuit 43 is comprised by an operational amplifier 57 and a feedback switching element 59. The operational amplifier 57 acts to prevent switching noise of the switching element 59 from riding on the output of the I-V converter circuit 24.

Figure 15:
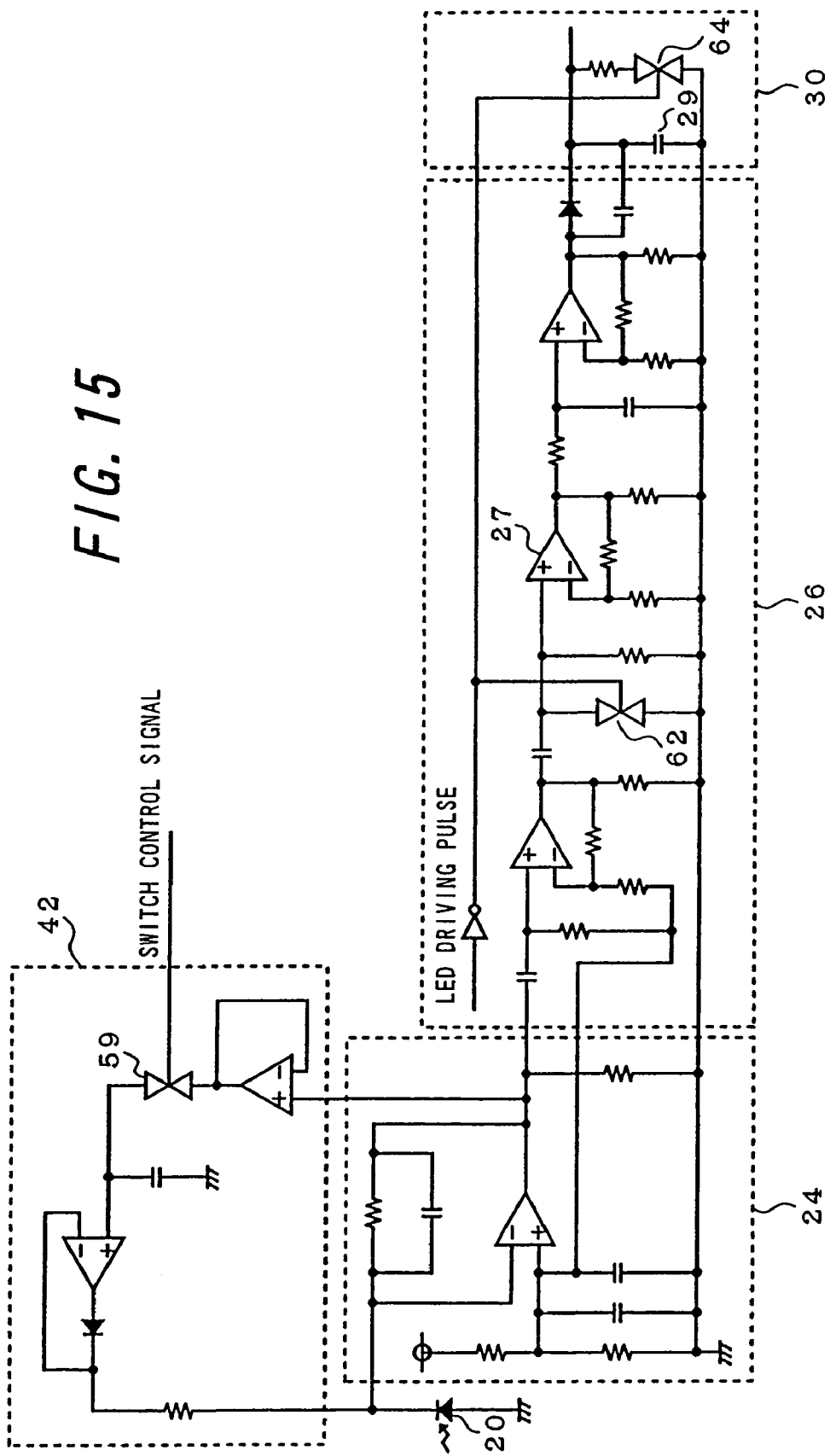
FIG. 15 is a concrete circuit diagram of a signal circuit provided with the outside-light component reducing circuit shown in FIG. 14.

FIG. 15 is a concrete circuit diagram of the signal detecting circuit provided with the outside-light component reducing circuit 42 shown in FIG. 14. Only the difference from the circuit shown in FIG. 10 is the outside-light component reducing circuit 42, while the V-I converter circuit 24, the band-pass filter circuit/amplifier circuit 26 and the peak hold circuit 30 are the same as in FIG. 10.

Turning on/off of the switching element 59 of the outside-light component reducing circuit 42 is controlled by a feedback switch control signal, which will be described later.

Figure 16:
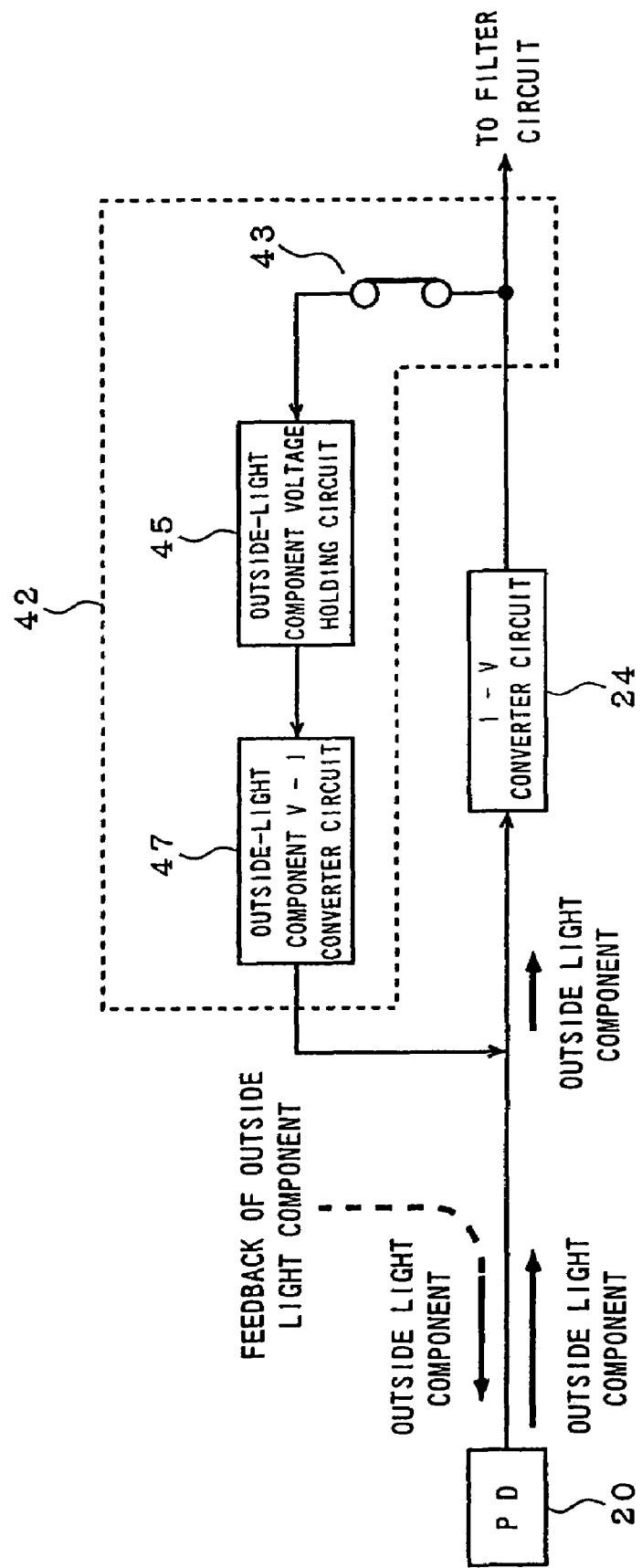
Figure 17:
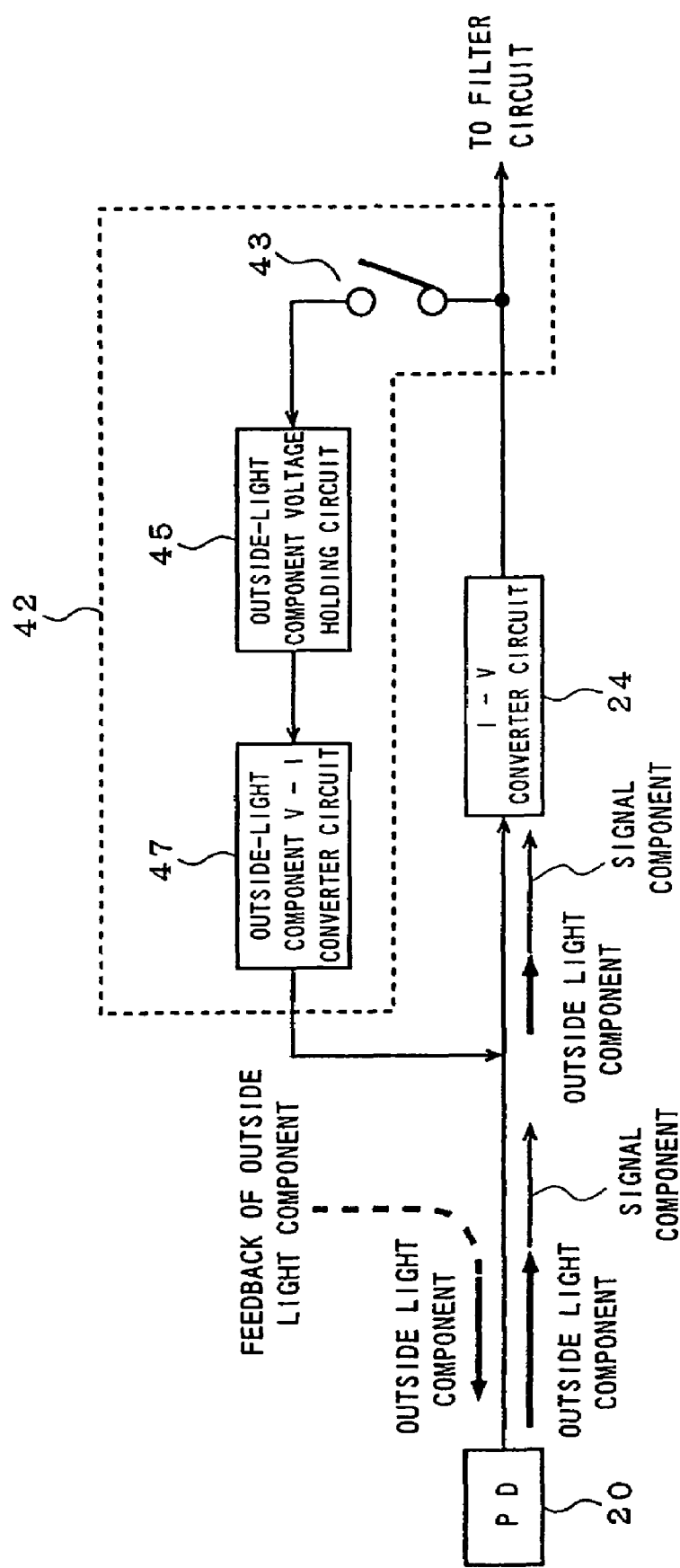
FIG. 17 is a diagram for explaining absence of taking-in of an outside light component voltage by turning a switch circuit off.

Next, operation of the outside-light component reducing circuit 42 according to this preferred embodiment will be described. FIGS. 16 and 17 are diagrams for explaining presence/absence of taking-in of the outside-light component voltage by turning on/off of the switch circuit 43.

Figure 18:
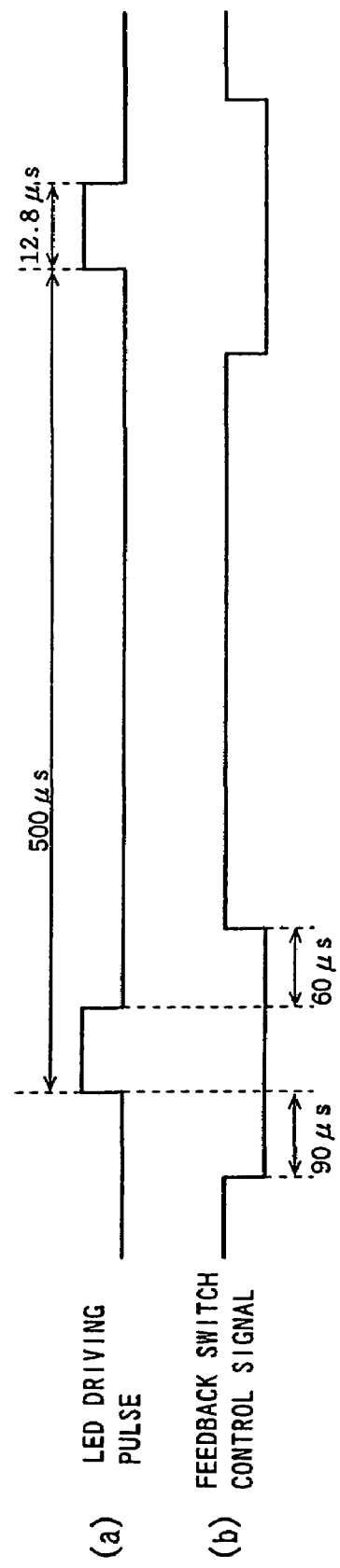
FIG. 18 is a diagram showing a timing of an LED lighting/driving pulse and a feedback switch control signal.

FIG. 18 is a diagram showing the timing between an LED lighting/driving pulse and a feedback switch control signal. (a) shows the waveform of the LED driving pulse and (b) for the waveform of the feedback switch control signal.

As shown in the waveform (a) in FIG. 18, the driving pulse for lighting the LED has the cycle of 500 μs and the pulse width of 12.8 μs. The LED 10 is lighted when the driving pulse is at H level and turned off at L level. Therefore, the pulse signal from the PD 20 is outputted in accordance with the driving pulse of the LED 10.

As shown in waveform (b) in FIG. 18, the feedback switch control signal is at the L level for the period including before and after the period when the LED lighting/driving pulse is at the H level, while it is at the H level in the other periods. As one example, the prior period is 90 μs and the post period is 60 μs. These periods are somewhat varied due to interrupt processing of the microcomputer 32.

As shown in FIG. 16, when the LED 10 is off, the feedback switch circuit 43 is turned on by the feedback switch control signal, and the outside-light component voltage is held in the capacitor 55 of the outside-light component voltage holding circuit 45. The held outside-light component voltage is converted to an electric current by the outside-light component V-I converter circuit 47 and fed back to the input side of the I-V converter circuit 24. The fed-back outside-light component current flows in the direction opposite to that of the pulse signal current from the PD, and only the reduced outside-light component current is inputted to the input of the I-V converter circuit 24.

Next, as shown in FIG. 17, when the LED 10 is on, the feedback switch circuit 43 is turned off by the feedback switch control signal, and the signal component outputted by the I-V converter circuit 24 is not taken in. That is because the signal component should not be fed back. Since the outside-light component voltage is held in the capacitor 55 of the outside-light component voltage holding circuit 45, the outside light component is fed back even during this period. Therefore, (reduced outside light component)+(signal component) is inputted to the I-V converter circuit 24.

Figure 19:
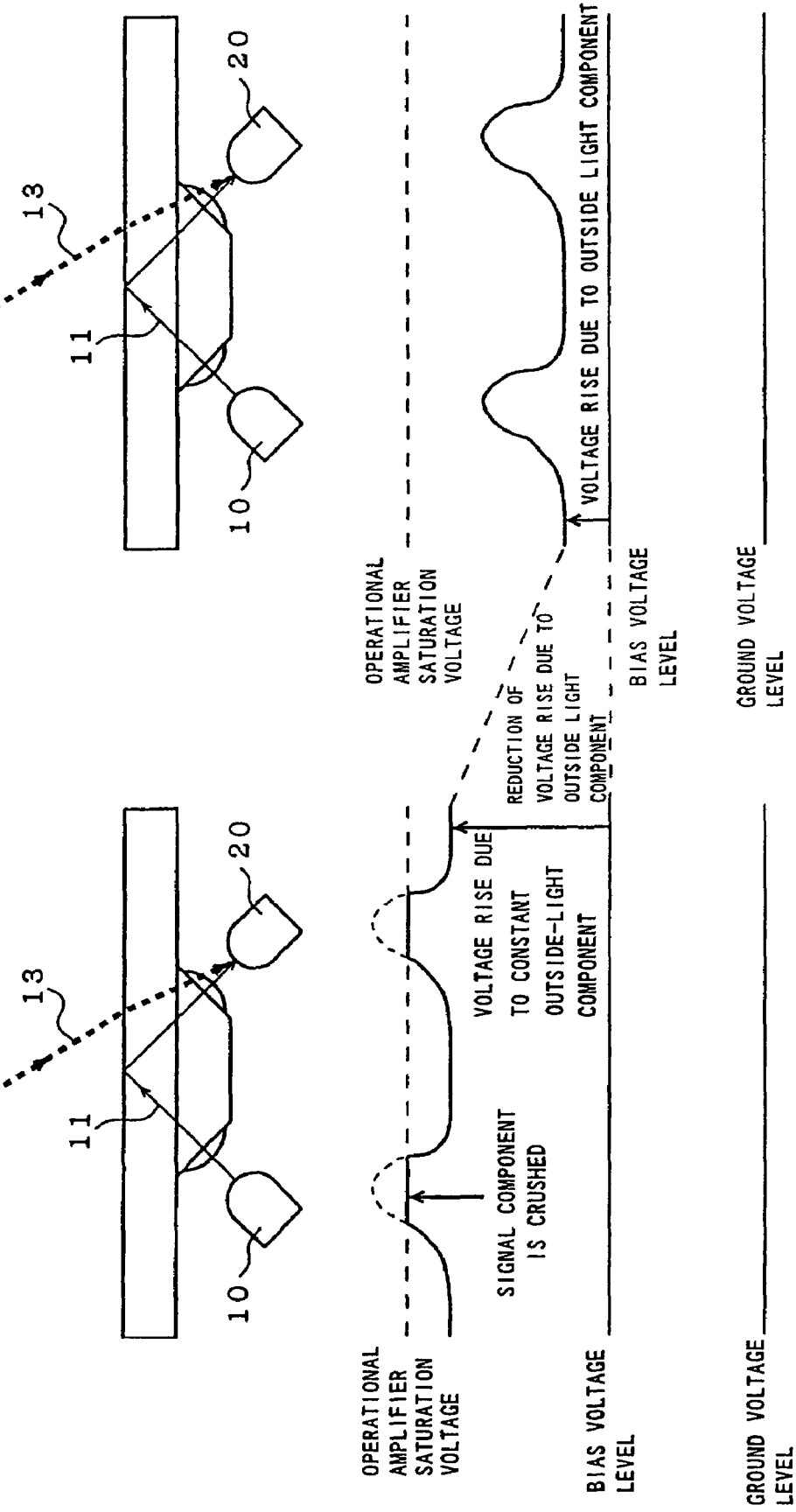
FIG. 19 is a diagram showing the effect of the outside-light component reducing circuit in comparison between the case where there is a circuit and the case where there is not.

FIG. 19 shows the effect of the outside-light component reducing circuit in comparison between the case with the circuit and the case without it. The diagram on the left in FIG. 19 shows the output signal waveform of the I-V converter circuit 24 when there is an outside light component and no outside-light component reducing circuit, while the diagram on the right shows the output signal waveform of the I-V converter circuit 24 when there are both an outside light component and the outside-light component reducing circuit.

If the outside-light component reducing circuit is not provided, it is known that the signal component is crushed when the saturation voltage of the operational amplifier of the I-V converter circuit 24 is exceeded by the voltage rise due to the outside light component.

If the outside-light component reducing circuit is provided, it is known that the outside light component is reduced and then, the saturation voltage of the operational amplifier is not exceeded and the signal component is not crushed.

The above is for the case where the outside light component is almost constant. The outside light component includes not only the constant outside-light component but also the fluctuating outside light component whose light intensity is fluctuated.

Figure 5:
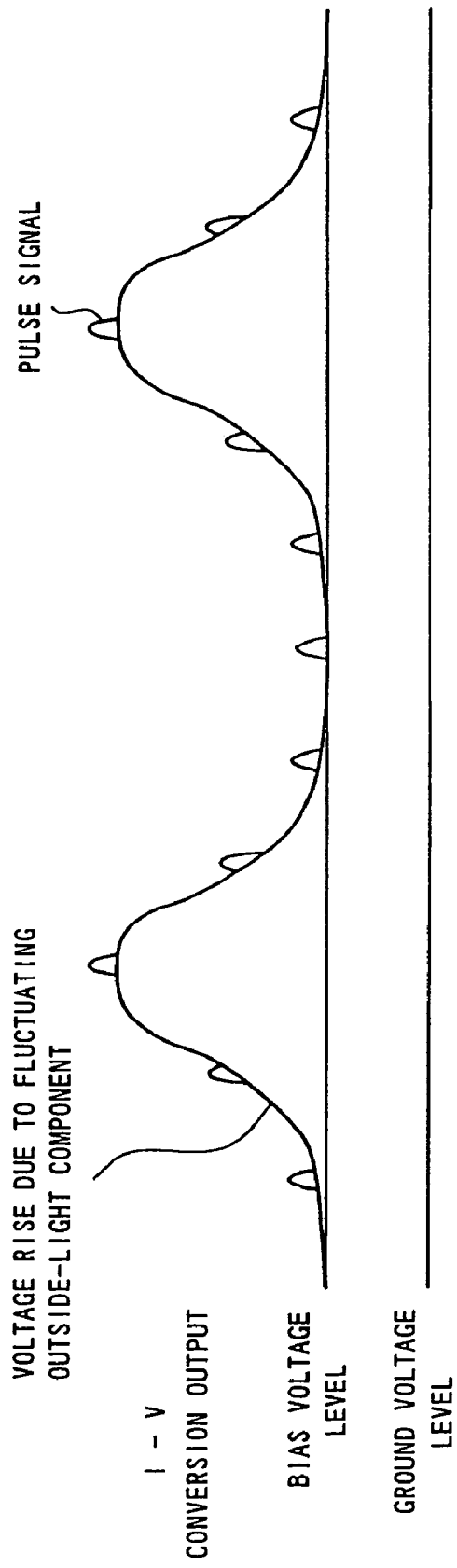
FIG. 5 is a diagram showing a pulse signal waveform from a PD when a fluctuating outside-light component exists.
Figure 6:
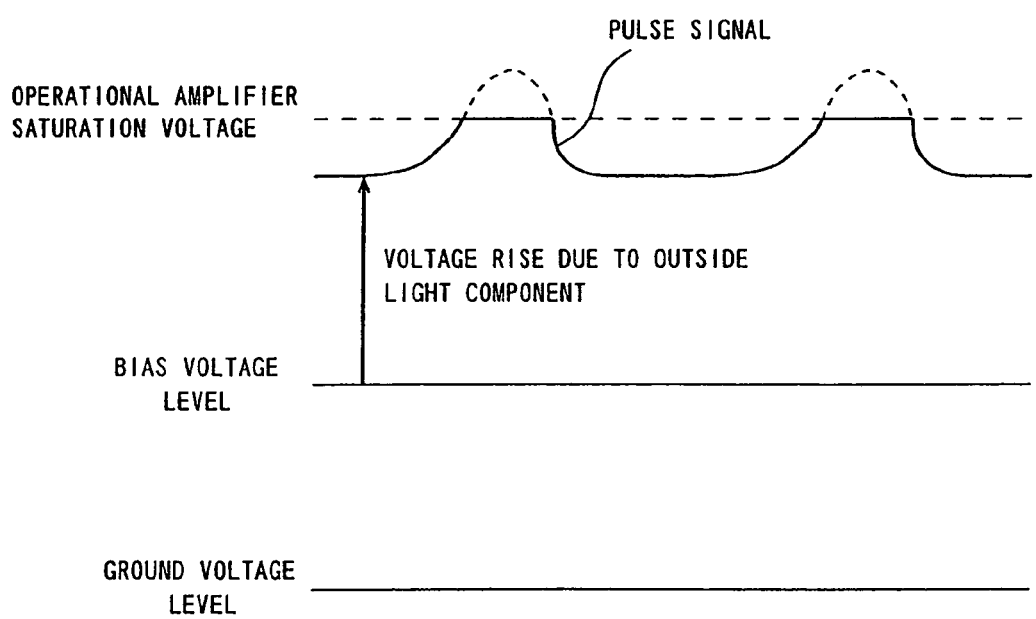
FIG. 6 is a diagram showing a pulse signal waveform from a PD when a constant outside-light component exists.
Figure 20:
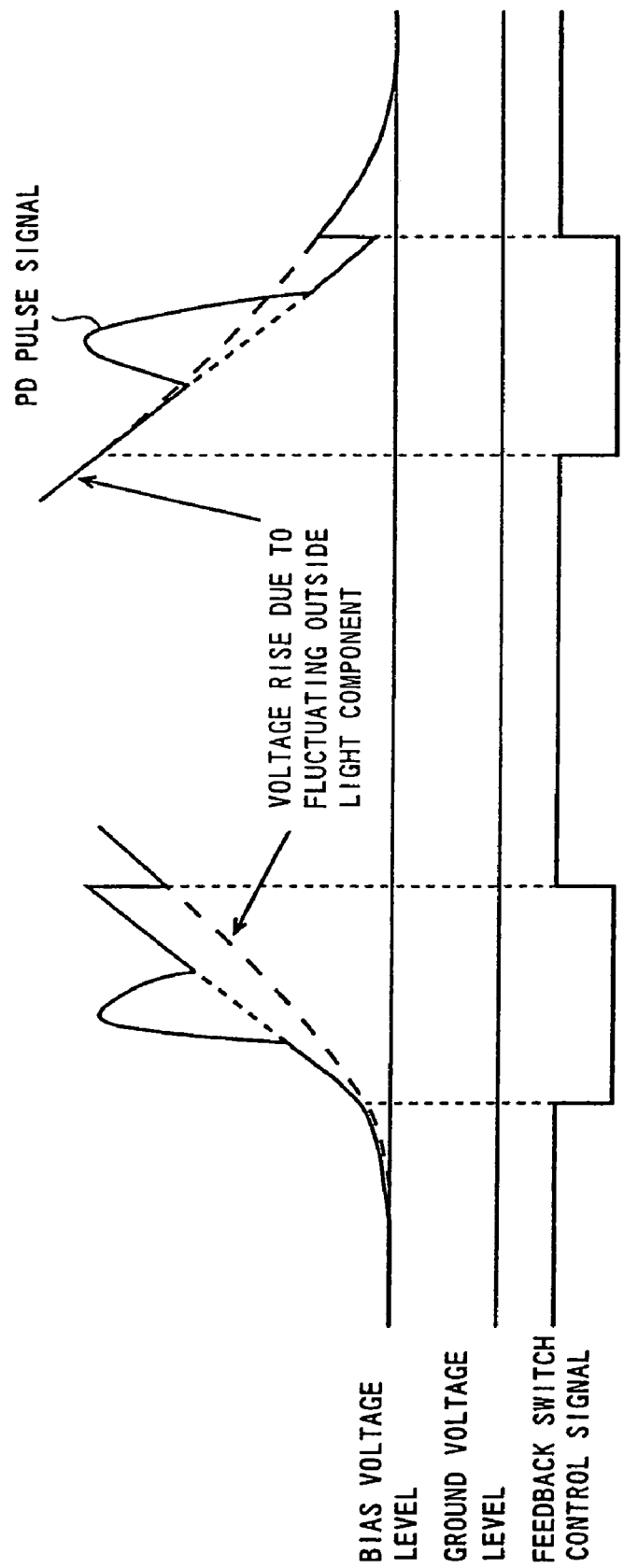
FIG. 20 is a diagram showing the state where the inclination of the fluctuating outside-light component becomes steep.

If the PD pulse signal whose voltage is raised by the fluctuating outside-light component shown in FIG. 5 is inputted in the I-V converter circuit 24 in FIG. 14, when the switching element 59 of the outside-light component reducing circuit 42 is turned off, as shown in FIG. 20, the inclination of the fluctuating outside-light component becomes steep. The steep inclination of the fluctuating outside-light component means that the fluctuating outside-light component includes higher frequency components.

Figure 21:
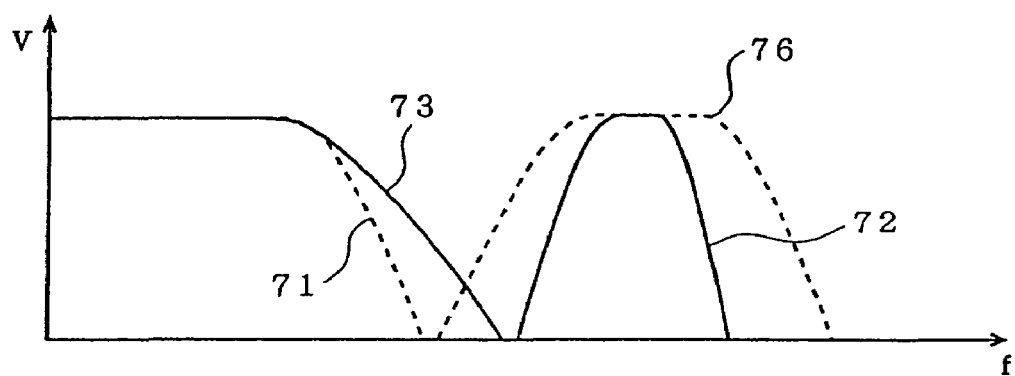
FIG. 21 is a diagram showing a relationship between the band of the fluctuating outside light component at on/off of the switch element of the outside-light component reducing circuit and a signal pass band of the band-pass filter circuit/amplifier circuit.

FIG. 21 shows the relationship between the band of the fluctuating outside-light component at on/off of the switching element 59 of the outside-light component reducing circuit 42 and the signal pass band of the band-pass filter circuit/amplifier circuit 26. Fig. also shows the PD pulse signal band. The vertical axis indicates the intensity of a signal component (V) and the horizontal axis for a frequency (f).

The band of the fluctuating outside-light component is expanded toward the high frequency side from 71 to 73 when the switching element 59 is switched from on to off. As a result, the high-frequency component of the fluctuating outside-light component enters the pass band 76 of the band-pass filter circuit/amplifier circuit 26, and then, the high-frequency component of the fluctuating outside-light component passes through the band-pass filter circuit/amplifier circuit and is outputted. Thus, the S/N ratio is deteriorated. In FIG. 21, 72 indicates the band of the PD pulse signal.

Figure 22:
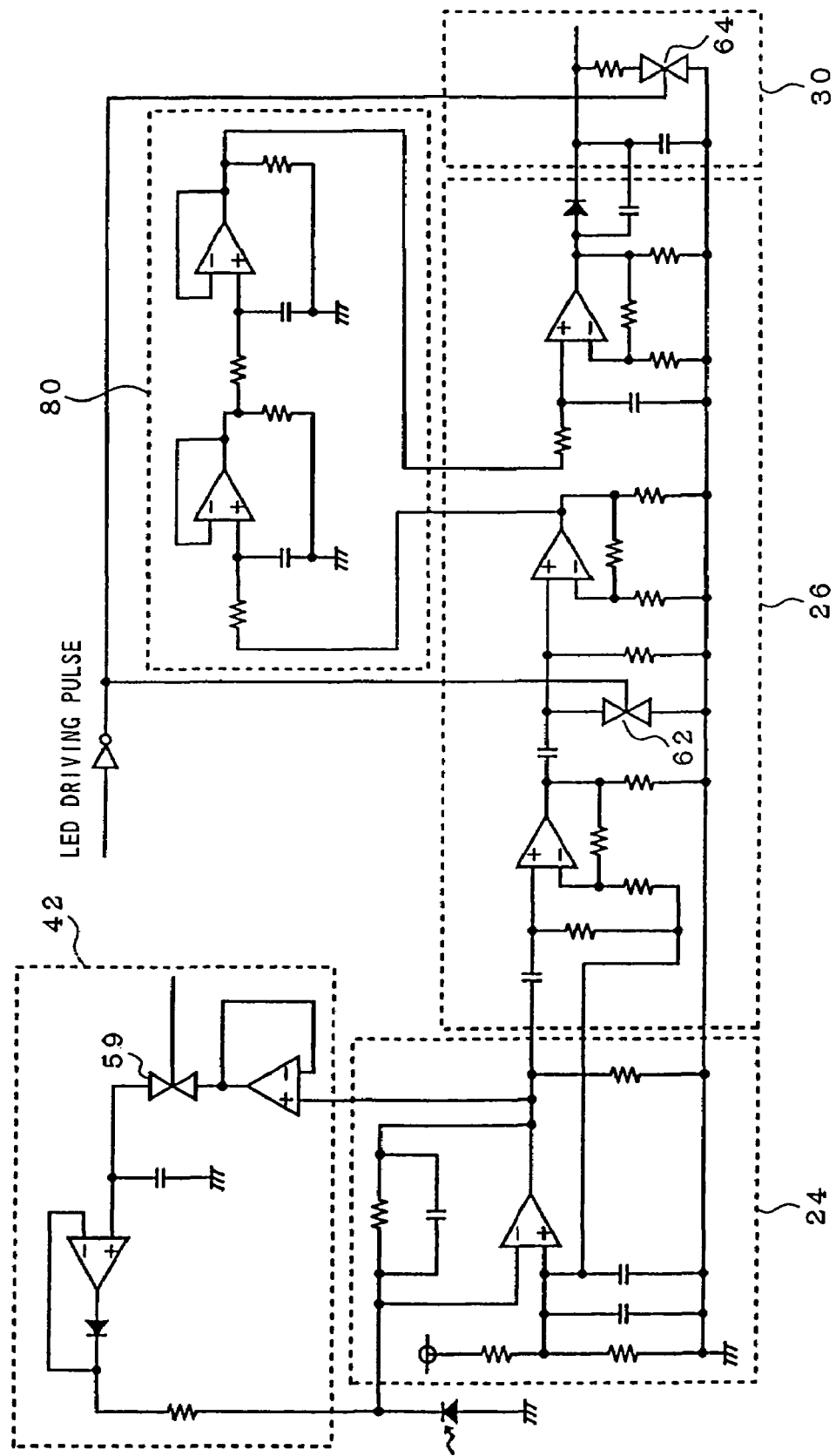
FIG. 22 is a graph showing a signal detecting circuit to which a circuit for eliminating a high-frequency noise by the fluctuating outside-light component is further added.
Figure 23:
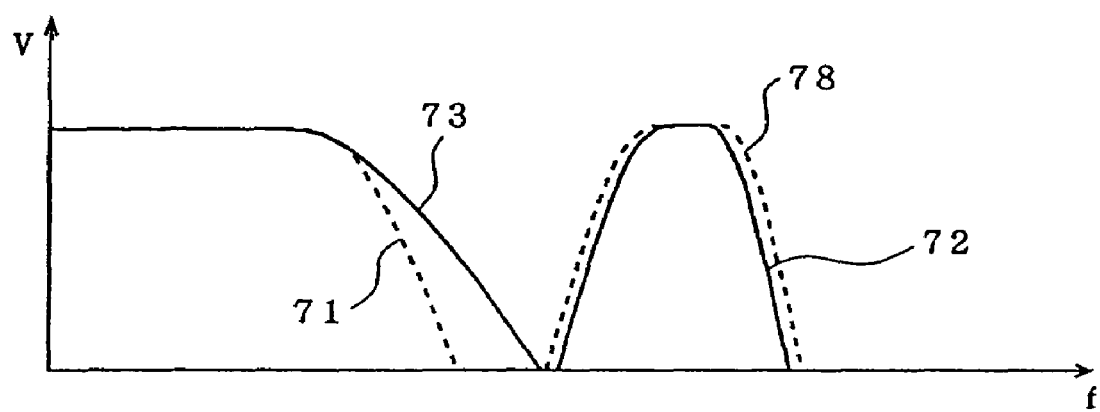
FIG. 23 is a diagram of the pass band to which the band-pass filter circuit/amplifier circuit with a low-pass filter circuit inserted is combined.

A signal detecting circuit to which such a circuit to eliminate high-frequency noise by the fluctuating outside-light component is added is shown in FIG. 22. This is a structure in which a fluctuating outside-light noise reducing circuit 80 is provided in the signal path of the band-pass filter circuit/amplifier circuit 26 in FIG. 15. This noise reducing circuit 80 has such a construction that low-pass filter circuits are connected in two stages. When such a low-pass filter circuit is inserted in the band-pass filter circuit/amplifier circuit 26, as shown in FIG. 23, the composite pass band is narrowed as 78 in the equivalent manner.

Therefore, the high frequency component of the fluctuating outside light is reduced, and the S/N ratio is improved.

INDUSTRIAL APPLICABILITY

According to the present invention, since an outside-light component reducing circuit is provided in a signal detecting circuit of a rain sensor, saturation of output of the I-V converter circuit due to the outside light component can be prevented and noise caused by the outside light component can be reduced. Therefore, an accurate signal can be inputted in a microcomputer, whereby more accurate rainfall level can be determined.

The invention claimed is:

1. A signal detecting circuit which irradiates a pulse light from a light emitting element to a windshield of a vehicle, receives a reflected light by a light receiving element, processes the pulse signal from the light receiving element and inputs it to a processing unit in order to control a wiper of the vehicle, comprising:
    a current—voltage converter circuit for converting the pulse signal from said light emitting element to a voltage signal;
    an outside-light component reducing circuit provided in parallel with said current—voltage converter circuit for holding a constant outside light component included in an output signal of said current—voltage converter circuit and feeding it back to the input side of said current—voltage converter circuit; and
    a band-pass filter circuit/amplifier circuit for reducing a noise of the output signal of said current—voltage converter circuit and for amplifying the output signal;
    wherein said outside-light component reducing circuit includes
    a switch circuit connected to the output side of said current—voltage converter circuit,
    an outside-light component voltage holding circuit connected to said switch circuit for holding the voltage of said constant outside light component, and
    an outside-light component voltage-current converter circuit connected to said outside-light component holding circuit for converting the held voltage to an electric current and feeding it back to the input side of said current—voltage converter circuit.

2. A signal detecting circuit according to claim 1, wherein a low-pass filter circuit is further provided inside said band-pass filter circuit/amplifier circuit for reducing a high frequency component of a fluctuating outside-light component included in the output signal.

3. A signal detecting circuit according to claim 1 or 2, wherein said switch circuit is turned on when said light emitting element is turned off, and
    said switch circuit is turned off when said light emitting element is turned on.

4. A signal detecting circuit according to claim 1 or 2, wherein said light emitting element is a light emitting diode, and said light receiving element is a photodiode.

5. An outside-light component reducing circuit in a Signal detecting circuit which irradiates a pulse light from a light emitting element to a windshield of a vehicle, receives a reflected light by a light receiving element, processes a pulse signal from the light receiving element and inputs it to a processing unit in order to control a wiper of the vehicle, for reducing said constant outside-light component, characterized in that the outside-light component reducing circuit is provided in parallel with a current—voltage converter circuit for converting the pulse signal from said light emitting element to a voltage signal for holding said constant outside light component included in an output signal of said current—voltage converter circuit and feeding it back to the input side of said current—voltage converter circuit,
    wherein said outside-light component reducing circuit further comprises:

a switch circuit connected to the output side of said current—voltage converter circuit;

an outside-light component voltage holding circuit connected to said switch circuit for holding the voltage of the constant outside light component; and an outside-light component voltage-current converter circuit connected to said outside-light component voltage holding circuit for converting the held voltage to an electric current and feeding it back to the input side of said current—voltage converter circuit.

6. An outside-light component reducing circuit according to claim 5, wherein said light emitting element is a light emitting diode and said light receiving element is a photodiode.

* * * * *